United States Patent [19]
Yamaura

[11] Patent Number: 5,951,469
[45] Date of Patent: Sep. 14, 1999

[54] REMOTE MEDICAL SYSTEM

[75] Inventor: Takahiro Yamaura, Fukuoka-ken, Japan

[73] Assignee: Medinet Security Research Co., Ltd., Fukuoka-ken, Japan

[21] Appl. No.: 09/144,461

[22] Filed: Sep. 1, 1998

[30]        Foreign Application Priority Data

Jun. 23, 1998   [JP]   Japan .................................. 10-176075

[51] Int. Cl.⁶ .................................................. A61N 5/04
[52] U.S. Cl. ......................................................... 600/300
[58] Field of Search ........................... 705/2, 3; 128/903, 128/904, 920, 924; 600/300, 301

[56]              References Cited

U.S. PATENT DOCUMENTS 5,704,366   1/1998   Tacklind et al. ..................... 128/904 X
5,827,180  10/1998   Goodman ................................. 600/300

*Primary Examiner*—Samuel Gilbert
*Attorney, Agent, or Firm*—Sughrue, Mion, Zinn, Macpeak & Seas, PLLC

[57]              ABSTRACT

A remote medical system in which vital signs and a recognition code of a counselee are transferred to a first local server through a telephone line, and, when a counseling doctor cannot be found, data is transferred to another nth local server to search for an available counseling doctor, so that an available counseling doctor can be easily found.

2 Claims, 1 Drawing Sheet

REMOTE MEDICAL SYSTEM

U.S. Patent  Sep. 14, 1999  5,951,469
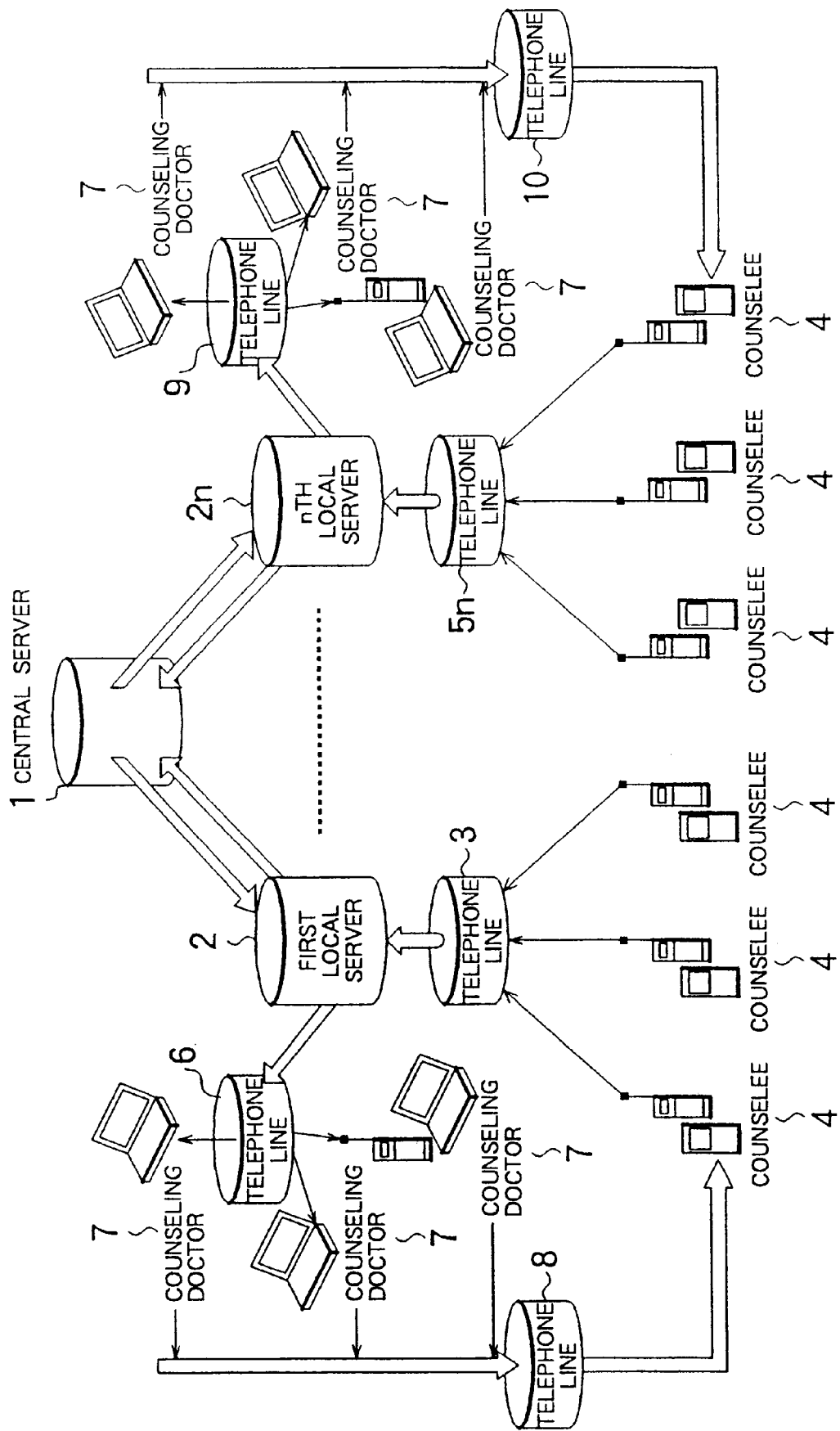

REMOTE MEDICAL SYSTEM

BACKGROUND OF THE INVENTION

1. Field of the Invention

The present invention relates to a remote medical system and, more particularly, to a novel improvement in which a load of a counseling doctor is reduced by using a telephone line and a plurality of local servers and a central server so that the counseling doctor can always quickly respond to a counselee.

2. Description of the Related Art

In a conventionally used remote medical system of this type, medical treatment is performed such that a counselee and a counseling doctor or a hospital are connected to exchange data with each other from remote locations in a one-to-one correspondence basis.

Since a conventional remote medical system is arranged as described above, the system has the following problem. Since a plurality of counselees (patients) are designated as corresponding to one counseling doctor (in charge of cases), the counseling doctor must diagnose the plurality of counselees and have a heavy load. In addition, a counselee must wait for the counseling doctor when the doctor is out or is on the phone, and in an emergency state, counseling may be too late.

SUMMARY OF THE INVENTION

The present invention has been made to solve the above problem and, more particularly, has as its object to provide a remote medical system which reduces a load of a counseling doctor by using a telephone line and a plurality of local servers and a central server so that the counseling doctor can always quickly respond to a counselee.

A remote medical monitoring method according to the present invention is a method comprising the steps of: transmitting vital signs and a recognition code of a counselee to a first local server through a telephone line; causing the first local server to search a primary counseling doctor, who is registered in advance, of the counselee using the transmitted recognition code to transfer data of the counselee to the counseling doctor; causing the first local server to check a counseling time table of a plurality of registered counseling doctors associated with the first local server when the primary counseling doctor is on the phone or is out so as to transfer the received data to another counseling doctor who can counsel the counselee; and causing the first local server to transfer the data to a central server when counseling doctors associated with the first local server who can counsel the counselee are on the phone or are out; and causing the central server to check the presence/absence of a counseling doctor who can counsel the counselee in a local server other than the first local server to transfer the data to a counseling doctor who can counsel the counselee.

BRIEF DESCRIPTION OF THE DRAWINGS

The FIGURE is a view showing the arrangement of a remote medical system according to the present invention.

DESCRIPTION OF THE PREFERRED EMBODIMENT

The following is a preferred embodiment of a remote medical system according to the present invention with reference to the accompanying drawings.

The FIGURE shows a remote medical system according to the present invention. Reference numeral 1 denotes a central server to which a plurality (n) of first through nth local servers, 2 through 2n are connected.

Counselees 4 serving as a plurality of patients or the like are connected to the first local server 2 through a first telephone line 3, and a plurality of counselees 4 are also connected to the nth local server 2n through a nth telephone line 5n.

A plurality of counseling doctors 7 associated with the first local server 2 are connected to the first local server 2 through another telephone line 6, and are also connected to the counselees 4 through another telephone line 8. The counseling doctors 7 associated with the nth local server 2n are connected to the nth local server 2n through other telephone lines 9 and 10 as described above. As the telephone lines, note only public telephone lines, but also private telephone lines may be used.

The operation of this system will be described below. The counselee (patient) 4 transmits vital signs (e.g., predetermined signals representing life support) of the counselee 4 and a recognition code (a code No. preset for each counselee) of the counselee 4 to the first local server 2 through the telephone line 3. The first local server 2 searches a primary counseling doctor 7, who is registered in advance, of the counselee from the transmitted recognition code to transfer data related to the diseases and body of the counselee 4 to the counseling doctor 7.

In the case described above, when the primary counseling doctor 7 is in a BUSY state, i.e., is on the phone or is out, the first local server 2 checks a counseling time table of a plurality of counseling doctors 7 who are registered in advance in the first local server 2 to transfer the received data to a counseling doctor 7 registered in the first local server and who can be in charge of this case. When the counseling doctors 7 who can be in charge of the case are in a BUSY state, i.e., are on the phone or are out in the first local server 2, the first local server 2 transfers the data to the central server 1, and the central server 1 checks the presence/absence of a counseling doctor 7 who can be in charge of the case. If the counseling doctor 7 is found, the data is transferred to the counseling doctor 7.

Therefore, the counselee 4 can rapidly find the counseling doctor 7 who is not busy by using the servers 1 and 2 through 2n. Since the counseling doctor 7 may counsel the counselee 4 only when the counseling doctor 7 is not busy, a load of the counseling doctor 7 can be reduced.

Since the remote medical system according to the present invention is arranged as described above, the following advantages can be achieved.

More specifically, each counselee automatically searches the non-busy state of a plurality of counseling doctors by using a local server and a central server. A counseling doctor registered in a server is only required to cope with a remote counseling when he or she is available. Therefore, the counselee can rapidly receive medical counseling service. In addition, a counseling doctor may counsel the counselee only when a plurality of counselees are not waiting. Accordingly, reductions in load of both the counselee and the counseling doctor and an increase in efficiency of information transmission can be achieved.

What is claimed is:

1. A remote medical monitoring method, comprising the steps of:

a) transmitting vital signs and a recognition code of a counselee to a first local server through a telephone line;

b) causing said first local server to identify a first counseling doctor of the counselee using the transmitted recognition code and causing said first local server to determine whether the first counseling doctor is available, wherein the first counseling doctor is registered as part of a first group of counseling doctors associated with said first local server;

c) transferring data of the counselee to the first counseling doctor when the first counseling doctor is available;

d) when the first counseling doctor is not available, causing said first local server to determine if a second counseling doctor who can counsel the counselee is available from the first group of counseling doctors;

e) transferring data of the counselee to the second counseling doctor when the second counseling doctor is available;

f) when all doctors of the first group of doctors are not available; causing the first local server to transfer the data to a central server; and g) causing said central server to locate an available counseling doctor in a second local server who can counsel the counselee so as to transfer the data of the counselee to the available counseling doctor in the second local server who can counsel the counselee.

2. A remote medical monitoring method, comprising the steps of:

a) transmitting data including a recognition code of a counselee to a first local server;

b) causing said first local server to identify a first counseling doctor of the counselee using the transmitted recognition code and causing said first local server to determine whether the first counseling doctor is available, wherein the first counseling doctor is registered with said first local server;

c) transferring the data of the counselee to the first counseling doctor when the first counseling doctor is available;

d) when the first counseling doctor is not available, causing said first local server to determine if a second counseling doctor who can counsel the counselee and who is registered with said first local server is available;

e) transferring the data of the counselee to the second counseling doctor when the second counseling doctor is available f) when there are no available counseling doctors who are registered with said first local server, causing the first local server to transfer the data to a central server; and g) causing said central server to locate an available counseling doctor in a second local server who can counsel the counselee so as to transfer the data of the counselee to the available counseling doctor in the second local server.

* * * * *